US007819963B2

(12) United States Patent
Kamohara et al.

(10) Patent No.: US 7,819,963 B2
(45) Date of Patent: Oct. 26, 2010

(54) DENTAL ALGINATE IMPRESSION MATERIAL COMPOSITION

(75) Inventors: Hiroshi Kamohara, Itabashi-ku (JP); Hiroki Morita, Itabashi-ku (JP)

(73) Assignee: GC Corporation, Tokyo (JP)

( * ) Notice: Subject to any disclaimer, the term of this patent is extended or adjusted under 35 U.S.C. 154(b) by 525 days.

(21) Appl. No.: 11/846,776

(22) Filed: Aug. 29, 2007

(65) Prior Publication Data

US 2008/0057465 A1 Mar. 6, 2008

(30) Foreign Application Priority Data

Sep. 6, 2006 (JP) .............................. 2006-241316

(51) Int. Cl.
*A61K 6/10* (2006.01)
(52) U.S. Cl. .................. 106/35; 433/214; 523/109; 523/115; 523/116; 523/118; 523/120; 524/28; 524/55; 524/423; 524/425; 524/448
(58) Field of Classification Search .................. 106/35, 106/205.2, 205.5; 523/109, 115, 116, 118, 523/120; 524/28, 55, 423, 425, 448; 433/214
See application file for complete search history.

(56) References Cited

U.S. PATENT DOCUMENTS

| 5,698,610 | A | * | 12/1997 | Futami et al. ............... 523/109 |
| 6,509,390 | B2 | * | 1/2003 | Watanabe et al. ........... 523/109 |
| 6,559,200 | B1 | * | 5/2003 | Kamohara et al. .......... 523/109 |
| 2006/0213396 | A1 | * | 9/2006 | Kamohara et al. ....... 106/157.2 |

* cited by examiner

*Primary Examiner*—C. Melissa Koslow
(74) *Attorney, Agent, or Firm*—Oblon, Spivak, McClelland, Maier & Neustadt, L.L.P.

(57) ABSTRACT

To provide a dental alginate impression material composition capable of solving a problem that the permeation rate of water with respect to the whole powder of an alginate impression material is slow at the time of use so that a kneading time is long and a sufficient operational time cannot be secured, and a problem that a kneaded material drops into a throat due to aging of the material at the time of taking an impression, the dental alginate impression material composition comprises 0.001 to 1% by weight of one or more kinds selected from oils mainly consisting of a fatty acid and an ester of alcohol, waxes mainly consisting of a fatty acid and an ester of glycerin, and a fatty acid ester; 0.01 to 10% by weight of a surfactant; and 0.01 to 10% by weight of one or more kinds of specific polysaccharides.

11 Claims, No Drawings

DENTAL ALGINATE IMPRESSION MATERIAL COMPOSITION

BACKGROUND OF THE INVENTION

1. Field of the Invention

The present invention relates to a dental alginate impression material composition used for taking the impression inside an oral cavity at the time of producing a prosthesis in a dental treatment.

2. Description of the Conventional Art

In a dental treatment, a dental alginate impression material has been widely used as an impression material for taking an impression of an oral cavity at the time of producing a prosthesis of a damaged portion in an oral cavity. Although an alginate impression material is a powder-like material or a paste-like material depending on the form of a product, a powder-like alginate impression material has been widely used since cost is low and an application area is wide. The present invention relates to the powder-like alginate impression material. Powder of an alginate impression material mainly include alginate, a gelatinizing reactant, a gelatinizing regulator, and a filler, and the powder is kneaded with water so as to be gelatinized and cured.

An alginate impression material is used by mixing and kneading powder with water so as to be gelatinized, taking it into an oral cavity, and curing it. At this time, the permeation speed of water with respect to the powder of an alginate impression material is slow, so that it takes much time to permeate water to the whole powder. Thus, since a kneading time is long, a sufficient operational time cannot be secured. Further, when powder of an alginate impression material is kept for a long period of time, the powder components are changed in quality with time. Thus, when such a material obtained by kneading powder of an alginate impression material with water is used in an oral cavity, the kneaded material easily drops. So, the dental impression material has a big problem that a kneaded material easily drops to a throat of a patient who faces up.

In order solve such problems, for example, Japanese Patent Application Laid Open No. 2002-104916 discloses a powder-like alginate impression material having excellent initial affinity for water, where the material includes bacillary diatomaceous earth, and polyoxyethylene aliphatic ether as a specific surfactant. However, this alginate impression material can improve initial affinity for water, but cannot improve the permeation speed of water, so that the kneading time is not shortened. Further, in order to solve the problem that an alginate impression material easily drops, an impression material including polysaccharides, such as carrageenan, pullulan, and the like, so as to make the material to hardly drop is disclosed, where the polysaccharides are also disclosed in the present invention. However, this invention improves the dropping problem of a material by a kneading condition (a ratio of powders to water), but does not solve a problem that a kneaded material drops due to aging.

SUMMARY OF THE INVENTION

A primary objective of the present invention is to provide a dental alginate impression material composition capable of solving a problem that a permeation speed of water with respect to the whole powder of an alginate impression material is slow at the time of using, so that a kneading time is long, and a sufficient operational time cannot be secured, and a problem that a kneaded material drops to a throat due to aging at the time of taking an impression.

The earnest work was carried out in order to solve the above-mentioned problems and, as a result of this, the followings were found out to complete the present invention. When an alginate impression material mainly including alginate, a gelatinizing reactant, a gelatinizing regulator and a filler further includes a specified material basically having hydrophobicity and a surfactant, the permeation speed of water with respect to the whole powder of an alginate impression material increases, so that a kneading time is shortened. Further, when an alginate impression material includes specified polysaccharides under existence of a specified hydrophobic material and a surfactant, a problem that a kneaded material easily drops due to aging of an alginate impression material can be solved.

That is, the present invention is an alginate impression material composition mainly comprising alginate, a gelatinizing reactant, a gelatinizing regulator, and a filler, in which the composition comprises 0.001 to 1% by weight of one or more kinds selected from oils mainly consisting of fatty acid and ester of alcohol, waxes mainly consisting of fatty acid and ester of glycerin, and fatty acid ester; 0.01 to 10% by weight of a surfactant; and 0.01 to 10% by weight of one or more kinds of polysaccharides selected from carrageenan, pullulan, curdlan, xanthan gum, gellan gum, pectin, konjak glucomannan, xyloglucan, guar gum, gum Arabic and locust bean gum.

According to a dental alginate impression material composition regarding to the present invention, since a permeation speed of water with respect to the whole powder of an alginate impression material is increased, a kneading time is short, and a material obtained by kneading an alginate impression material and water does not easily drop due to aging.

DETAILED DESCRIPTION OF PREFERRED EMBODIMENT

An alginate impression material composition according to the present invention mainly comprising general alginate, a gelatinizing reactant, a gelatinizing regulator, and a filler, in which the composition further comprises one or more kinds of basically hydrophobic components selected from oils mainly consisting of fatty acid and ester of alcohol, waxes mainly consisting of a fatty acid and ester of glycerin, and fatty acid ester, a surfactant, and one or more kinds of polysaccharides selected from carrageenan, pullulan, curdlan, xanthan gum, gellan gum, pectin, konjak glucomannan, xyloglucan, guar gum, gum Arabic and locust bean gum.

For example, the oils are a palm oil, a camellia oil, a coconut oil, and the like, which mainly include fatty acid and ester of alcohol. For example, the waxes are lanolin mainly including fatty acid and ester of glycerin. For example, the fatty acid ester is glyceryl tetraoleate, glyceryl isostearate, or the like, which includes a fatty acid and an ester of alcohol.

The one or more kinds of materials selected from the oils mainly including fatty acid and ester of alcohol, the waxes mainly including a fatty acid and ester of glycerin, and the fatty acid ester can be used independently or by combining them. Among the materials, lanolin is the most preferable.

The content of one or more kinds of materials selected from the oils mainly including a fatty acid and an ester of alcohol, the waxes mainly including a fatty acid and an ester of glycerin, and the fatty acid ester is necessarily 0.001 to 1% by weight in the composition. If the content is less than 0.001% by weight or more than 1% by weight, the permeation speed of water with respect to the whole powder of an alginate impression material cannot be increased even when these materials are mixed with a surfactant described below, and the effect to suppress easily dropping of a kneaded material due to aging cannot be obtained. Preferably, the content is 0.01 to 0.1% by weight.

A surfactant is preferably a nonionic surfactant, and it is preferable to use a nonionic surfactant including an alkyl group such as polyoxyethylene alkylphenyl ether, polyoxyethylene/polyoxypropylene alkyl ether, polyoxyethylene alkyl ether, or the like. Further, an alkyl group having an average carbon number of 14.2 to 14.7 is the most preferable. More particularly, as polyoxyethylene alkyl ether, "NAROACTY-N", "NAROACTY-HN", and "NAROACTY-CL", which are produced by Sanyo Chemical Industries Corporation, can be used. These surfactants have high effect since those have a lower molecular weight distribution of polyoxyethylene chain than that of the other surfactants.

It is necessary to contain 0.01 to 10% by weight of the surfactant in the composition. If the content is less than 0.01% by weight, the above-described effect is not enough, and if the content is more than 10% by weight, storage stability of a composition decreases, so that a kneaded material easily drops due to aging. More preferably, the content is 0.05 to 1% by weight.

One or more kinds of polysaccharides selected from carrageenan, pullulan, curdlan, xanthan gum, gellan gum, pectin, konjak glucomannan, xyloglucan, guar gum, gum Arabic and locust bean gum are combined with one or more kinds of the materials selected from the oils mainly including a fatty acid and an ester of alcohol, the waxes mainly including a fatty acid and an ester of glycerin, and a fatty acid ester, and the surfactant. According to this combination, it can be prevented that a kneaded material of an alginate impression material easily drops, and a problem that the material easily drops due to aging can be solved. The polysaccharides can be used independently or by combining one or more kinds. Among the polysaccharides, carrageenan, xanthan gum and guar gum are preferable.

It is necessary to blend 0.01 to 10% by weight of the polysaccharides in the composition. If the amount is less than 0.01% by weight, a kneaded material easily drops, and if the amount is more than 10% by weight, viscosity of a kneaded material becomes remarkably high, so that it is hard to knead the material and take an impression. More preferably, the blending amount is within the range of 0.1 to 2% by weight. If the amount is within this range, an alginate impression material having the most proper flowability as a kneaded material can be obtained.

Of course, the dental alginate impression material composition can include a publicly known additive such as a colorant, a perfume, and the like, a publicly known various kinds of fluorides or a magnesium compound in order to decrease a roughness of a gypsum surface, publicly known hydrocarbon to suppress dust of powder, and a publicly known antibacterial agent. These materials can be used within the range not to damage the effect of the present invention.

EXAMPLE

The present invention will be described in details below with reference to examples, but the present invention is not limited in these examples.

Example 1

| | |
|---|---|
| Sodium alginate (Alginate): | 12% by weight |
| Calcium sulfate dihydrate (Gelatinizing reactant): | 12% by weight |
| Sodium pyrophosphate decahydrate (Gelatinizing regulator): | 2% by weight |
| Diatomaceous earth (Filler): | 71.17% by weight |
| Lanolin (Waxes): | 0.03% by weight |
| Polyoxyethylene alkyl ether (Surfactant): | 0.3% by weight |
| Xanthan gum (Polysaccharides): | 0.5% by weight |
| Fluoridation potassium titanate (Fluoride): | 1% by weight |
| Liquid paraffin (Hydrocarbon): | 1% by weight |

Powder of an alginate impression material composition was obtained by fully mixing the above-described components by a mixer.

<Measuring of Initial Curing Time>

A permeation speed of water with respect to the whole powder of the mixture and a kneading time were measured by the steps of weighing 16.8 g of the powder, taking it into a rubber cup, weighing 40 cc of water, taking it into the rubber cup in which the powder was taken in, beginning to mix the mixture and water by a spatula immediately after taking the water, measuring a time to permeate water to the whole powder. After 15 seconds from the beginning of kneading, kneading was finished and the initial curing time was measured based on "JIS T6505". Then, in the same manner as the above, initial curing times when kneading was done for 15 seconds, 25 seconds and 35 seconds were measured. These results were shown in Table 1.

<Measuring of Flow>

Expansion of the kneaded material by its own weight was measured in order to evaluate easiness of dropping. The easiness of dropping of the kneaded material was measured by the steps of filling the materials, which were kneaded for 15 seconds, 25 seconds, and 35 seconds from beginning of kneading like the above-described test, into metal rings having an inner diameter of 35 mm and a height of 50 mm, pushing out only the compositions onto a glass plate after 60 seconds from beginning of kneading, curing them, measuring diameters of expansion of the kneaded materials, and using the measured diameters as flow values substituting for property of an easiness of dropping. These results were shown in Table 1.

<Confirming of Change Due to Aging>

Change of a flow value due to aging was evaluated by the steps of filling 1 kg of the powder of an alginate impression material composition into an aluminum pack, storing it for 1 week at 60 degree C. and 100% humidity, measuring a flow value again, and confirming the change of a flow value with that before being stored. These results were shown in Table 1.

Example 2

| | |
|---|---|
| Sodium alginate (Alginate): | 11% by weight |
| Calcium sulfate dihydrate (Gelatinizing reactant): | 13% by weight |
| Sodium pyrophosphate decahydrate (Gelatinizing regulator): | 2% by weight |
| Diatomaceous earth (Filler): | 70.14% by weight |
| Lanolin (Waxes): | 0.06% by weight |
| Polyoxyethylene alkyl ether (Surfactant): | 0.8% by weight |
| Xanthan gum (Polysaccharides): | 1% by weight |
| Fluoridation potassium titanate (Fluoride): | 1% by weight |
| Liquid paraffin (Hydrocarbon): | 1% by weight |

Powder of an alginate impression material composition was obtained by fully mixing the above-described components by a mixer. The composition was subjected to similar tests to those of Example 1. The results were shown in Table 1.

Example 3

| | |
|---|---|
| Sodium alginate (Alginate): | 12% by weight |
| Calcium sulfate dihydrate (Gelatinizing reactant): | 12% by weight |
| Sodium pyrophosphate decahydrate (Gelatinizing regulator): | 2% by weight |
| Diatomaceous earth (Filler): | 71.79% by weight |
| Lanolin (Waxes): | 0.01% by weight |
| Polyoxyethylene alkyl ether (Surfactant): | 0.1% by weight |
| Xanthan gum (Polysaccharides): | 0.1% by weight |
| Fluoridation potassium titanate (Fluoride): | 1% by weight |
| Liquid paraffin (Hydrocarbon): | 1% by weight |

Powder of an alginate impression material composition was obtained by fully mixing the above-described components by a mixer. The composition was subjected to similar tests to those of Example 1. The results were shown in Table 1.

Example 4

| | |
|---|---|
| Sodium alginate (Alginate): | 12% by weight |
| Calcium sulfate dihydrate (Gelatinizing reactant): | 12% by weight |
| Sodium pyrophosphate decahydrate (Gelatinizing regulator): | 2% by weight |
| Diatomaceous earth (Filler): | 65.5% by weight |
| Lanolin (Waxes): | 0.5% by weight |
| Polyoxyethylene nonylphenyl ether (Surfactant): | 3.0% by weight |
| Guar gum (Polysaccharides): | 3.0% by weight |
| Fluoridation potassium titanate (Fluoride): | 1% by weight |
| Liquid paraffin (Hydrocarbon): | 1% by weight |

Powder of an alginate impression material composition was obtained by fully mixing the above-described components by a mixer. The composition was subjected to similar tests to those of Example 1. The results were shown in Table 1.

Comparative Example 1

| | |
|---|---|
| Sodium alginate (Alginate): | 12% by weight |
| Calcium sulfate dihydrate (Gelatinizing reactant): | 12% by weight |
| Sodium pyrophosphate decahydrate (Gelatinizing regulator): | 2% by weight |
| Diatomaceous earth (Filler): | 71.4% by weight |
| Lanolin (Waxes): | 0.1% by weight |
| Guar gum (Polysaccharides): | 0.5% by weight |
| Fluoridation potassium titanate (Fluoride): | 1% by weight |
| Liquid paraffin (Hydrocarbon): | 1% by weight |

Powder of an alginate impression material composition was obtained by fully mixing the above-described components by a mixer. The composition was subjected to similar tests to those of Example 1. The results were shown in Table 1.

Comparative Example 2

| | |
|---|---|
| Sodium alginate (Alginate): | 12% by weight |
| Calcium sulfate dihydrate (Gelatinizing reactant): | 12% by weight |
| Sodium pyrophosphate decahydrate (Gelatinizing regulator): | 2% by weight |
| Diatomaceous earth (Filler): | 71.5% by weight |
| Polyoxyethylene nonylphenyl ether (Surfactant): | 0.5% by weight |
| Fluoridation potassium titanate (Fluoride): | 1% by weight |
| Liquid paraffin (Hydrocarbon): | 1% by weight |

Powder of an alginate impression material composition was obtained by fully mixing the above-described components by a mixer. The composition was subjected to similar tests to those of Example 1. The results were shown in Table 1.

TABLE 1

| | | | Examples | | | | Comparative Examples | |
|---|---|---|---|---|---|---|---|---|
| | | | 1 | 2 | 3 | 4 | 1 | 2 |
| Permeation Time of Water (second) | | | 5 | 4 | 5 | 5 | 12 | 10 |
| Initial Curing Time (second) | Kneading Time (second) | 15 | 130 | 125 | 130 | 135 | 180 | 170 |
| | | 25 | 130 | 125 | 130 | 135 | 150 | 150 |
| | | 35 | 130 | 125 | 130 | 135 | 130 | 130 |
| Change Amount of Flow (mm) Note: Inside of ( ) is an initial flow value. | Kneading Time (second) | 15 | 0 (50) | 0.5 (51) | 0 (50) | 0.5 (50) | 6 (52) | 7 (60) |
| | | 25 | 0 (50) | 0.5 (51) | 0 (50) | 0.5 (50) | 5 (50) | 6 (57) |
| | | 35 | 0 (50) | 0.5 (51) | 0 (50) | 0.5 (50) | 5 (51) | 6 (57) |

Clearly seen from Table 1, as for dental alginate impression material compositions of the present invention shown in Examples, the permeation time of water is about 5 seconds, and thus water can permeate into the whole powder of an alginate impression material in a shorter time than that of Comparative Examples. The permeation time is about a half of that of Comparative examples. There is no difference at the initial curing time when kneading was done for 15 seconds, 25 seconds and 35 seconds from beginning of kneading. Thus, it is found out that the material is sufficiently kneaded even when the kneading time is short, e.g., 15 seconds. On the other hand, as for the compositions of Comparative Examples, it is found out that the difference due to kneading time is large When the kneading time is short, the initial curing time is long, that is, the material is not sufficiently kneaded. Further, the results of Examples shows that even when the material is kept under the conditions at 60 degree C. and 100% humidity for one week, there is few flow change, and the characteristic that the material does not initially drop is not influenced from a change due to aging.

What is claimed is:

1. An alginate impression material composition, comprising
    alginate,
    a gelatinizing reactant,
    a gelatinizing regulator,
    a filler,
    0.001 to 1% by weight of one or more oils selected from the group consisting of a fatty acid and an ester of alcohol,
    a wax selected from the group consisting of a fatty acid, an ester of glycerin, and fatty acid ester;
    0.01 to 10% by weight of a surfactant; and
    0.01 to 10% by weight of one or more polysaccharides selected from the group consisting of carrageenan, pullulan, curdlan, xanthan gum, gellan gum, pectin, konjak glucomannan, xyloglucan, guar gum, gum Arabic and locust bean gum.

2. The alginate impression material composition of claim 1, wherein the oil is palm oil, a camellia oil, or a coconut oil.

3. The alginate impression material composition of claim 1, wherein the wax is lanolin.

4. The alginate impression material composition of claim 1, comprising a fatty acid ester, which is glyceryl tetraoleate or glyceryl isostearate.

5. The alginate impression material composition of claim 1, wherein the surfactant is a nonionic surfactant.

6. The alginate impression material composition of claim 5, wherein the nonionic surfactant is polyoxyethylene alkylphenyl ether, polyoxyethylene/polyoxypropylene alkyl ether, or polyoxyethylene alkyl ether.

7. The alginate impression material composition of claim 1, wherein the one or more polysaccharides is selected from the group consisting of carrageenan, xanthan gum and guar gum.

8. The alginate impression material composition of claim 1, further comprising one or more additives selected from the group consisting of a colorant, a perfume, fluorides, magnesium compound, and an antibacterial agent.

9. A method of manufacturing the alginate impression material composition of claim 1, comprising mixing alginate, the gelatinizing reactant, the gelatinizing regulator, the filler, oils, wax, surfactant, and polysaccharides.

10. A method of making a dental impression, the method comprising providing the dental alginate impression material composition of claim 1 to the inside of an oral cavity to make a dental impression.

11. In a method of making a dental prosthesis, the improvement comprising making a dental impression with the dental alginate impression material composition of claim 1 in the inside of an oral cavity.

\* \* \* \* \*